United States Patent [19]

Perlin

[11] Patent Number: 4,517,984

[45] Date of Patent: * May 21, 1985

[54] ESOPHAGEAL PROBE

[75] Inventor: Alfred R. Perlin, Highland Park, Ill.

[73] Assignee: The Kendall Company, Boston, Mass.

[ * ] Notice: The portion of the term of this patent subsequent to Dec. 8, 1998 has been disclaimed.

[21] Appl. No.: 596,488

[22] Filed: Apr. 4, 1984

Related U.S. Application Data

[63] Continuation of Ser. No. 321,878, Nov. 16, 1981, , which is a continuation of Ser. No. 128,001, Mar. 7, 1980, abandoned.

[51] Int. Cl.$^3$ .............................................. A61B 5/02
[52] U.S. Cl. ............................ 128/642; 128/670; 128/715; 128/773; 128/780; 128/748
[58] Field of Search ............... 128/773, 715, 642, 748, 128/670, 780

[56] References Cited

U.S. PATENT DOCUMENTS

| | | | |
|---|---|---|---|
| 2,750,938 | 6/1956 | Bier | 128/715 X |
| 3,734,094 | 5/1973 | Calinog | 128/642 |
| 3,939,823 | 2/1976 | Kaye et al. | 128/748 |
| 3,951,136 | 4/1976 | Wall | 128/715 X |
| 4,072,056 | 2/1978 | Lee | 128/675 X |
| 4,176,660 | 12/1979 | Mylrea | 128/715 X |
| 4,214,593 | 6/1980 | Imbruce et al. | 128/748 |
| 4,304,239 | 12/1981 | Perlin | 128/773 |

OTHER PUBLICATIONS

Maxted et al., Med. & Biol. Eng. & Comput., vol. 15, 1977, pp. 398–401.
Shaw et al., Med. & Biol. Eng. and Comput., vol. 18, 1980, pp. 488–492.

Primary Examiner—Kyle L. Howell
Assistant Examiner—John C. Hanley
Attorney, Agent, or Firm—Powell L. Sprunger

[57] ABSTRACT

An esophageal probe comprising, a shaft assembly including an elongated shaft, and a sound conducting medium extending from a distal location of the shaft assembly to a proximal location of the shaft assembly. The probe has a vibration detection device adjacent a proximal portion of the medium to detect sounds transmitted by the medium.

4 Claims, 5 Drawing Figures

ESOPHAGEAL PROBE

This is a continuation of application Ser. No. 321,878, filed Nov. 16, 1981, as a continuation of Ser. No. 128,001, filed Mar. 7, 1980 now abandoned.

BACKGROUND OF THE INVENTION

The present invention relates to monitoring devices, and more particularly to esophageal probes.

An assortment of esophageal probes have been proposed for insertion into the esophagus of a patient to monitor body functions of the patient. However, in the past either the entire probe has been considered disposable resulting in a relatively large cost of the probe which is thrown away or the entire probe has been considered non-disposable resulting in inconvenience of handling of the probe, such as cleaning and sterilization between uses on separate patients.

SUMMARY OF THE INVENTION

A principal feature of the present invention is the provision of an improved esophageal probe for use in a patient.

The esophageal probe comprises, a shaft assembly having an elongated shaft with an inflation lumen extending through the shaft and communicating with an opening adjacent a distal end of the shaft. The shaft assembly has an inflatable balloon extending around the distal end of the shaft and defining a cavity communicating with the opening, and a first connector attached to the proximal end of the shaft, with the inflation lumen extending through the first connector to a proximal end of the first connector. The first connector has a flexible membrane closing a proximal end of the lumen adjacent a proximal end of the first connector, and valve means communicating with the inflation lumen to permit passage of liquid into the inflation lumen. The probe has a second connector having a vibration detection device, and means for releasably attaching the second connector to the first connector.

A feature of the present invention is that the valve means may be utilized to fill the inflation lumen with liquid and inflate the balloon.

Another feature of the invention is that the liquid in the inflation lumen and balloon cavity serves as a sound conducting medium in order to conduct sounds from the balloon to the proximal end of the first connector.

Another feature of the invention is that the vibration detection device is located adjacent the membrane when the second connector is attached to the first connector.

Thus, a feature of the present invention is that the vibration detection device detects sounds conducted through the liquid to the proximal membrane.

Yet another feature of the invention is that the vibration detection device is located in the second connector rather than the shaft, permitting a reduced diameter of the shaft for insertion into the patient.

A further feature of the invention is that the shaft assembly may be discarded after use on a patient, after which the second connector may be attached to another shaft assembly for use on a subsequent patient.

Thus, another feature of the invention is that the second connector including the vibration detection device may be utilized with a plurality of shaft assemblies in different patients to avoid necessity of discarding the relatively expensive vibration detection device while permitting discarding of the disposable shaft assembly.

Further features will become more fully apparent in the following description of the embodiments of this invention and from the appended claims.

DESCRIPTION OF THE PREFERRED EMBODIMENTS

Figure 1:
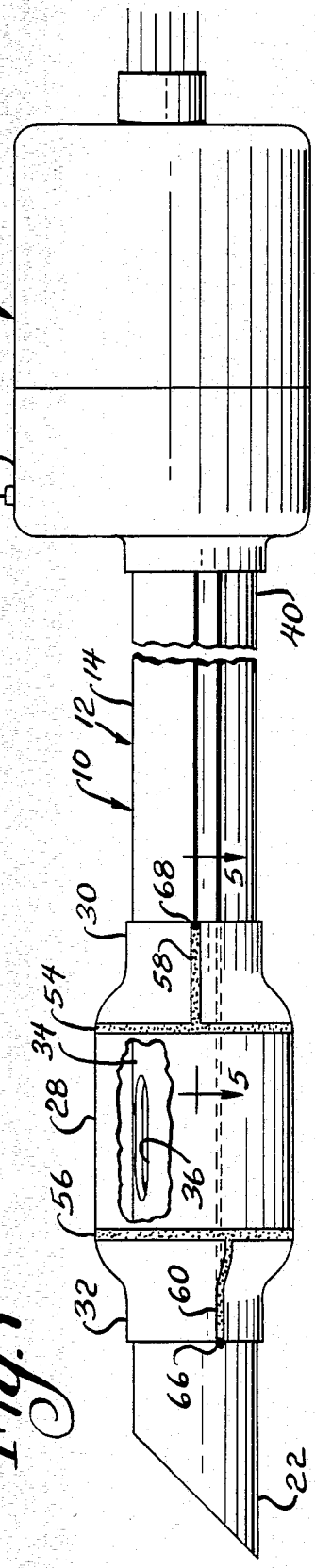
FIG. 1 is a fragmentary elevational view of an esophageal probe of the present invention.
Figure 5:
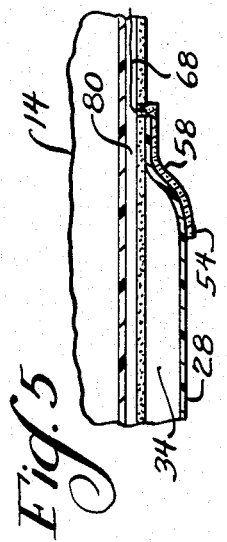
FIG. 5 is a fragmentary sectional view, taken substantially as indicated along the line 5—5 of FIG. 1.
Figure 2:
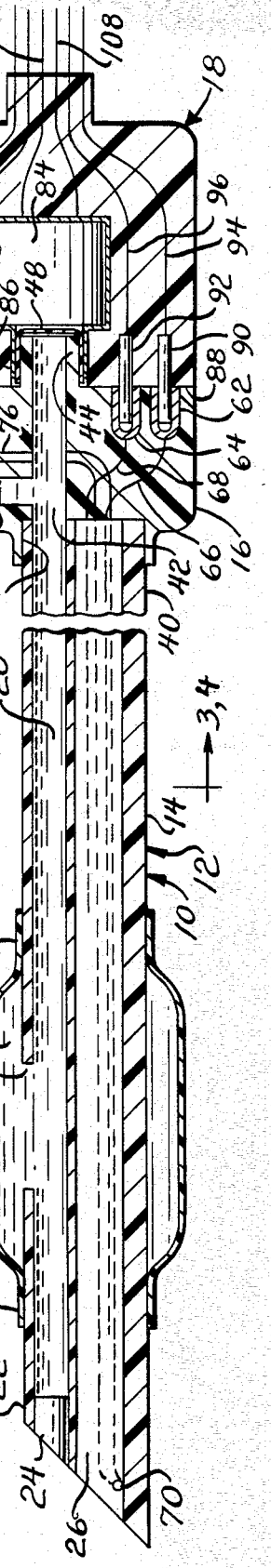
FIG. 2 is a fragmentary elevational view, taken partly in section, of the probe of FIG. 1.

Referring now to FIGS. 1 and 2, there is shown an esophageal probe generally designated 10 having a shaft assembly 12 comprising an elongated shaft 14 and proximal first connector 16, with the probe 10 also having a second proximal connector or plug 18. As shown, the shaft 14 has a first inflation lumen 20 extending through the shaft and being closed at a distal end 22 of the shaft by a suitable plug 24, and a second lumen 26 extending through the shaft. The shaft assembly 12 also has a cylindrical inflatable balloon 28 of elastic material having first and second opposed end portions 30 and 32 being secured to an outer surface of the shaft 14 in circumferential zones, such that the balloon 28 defines a cavity 34 communicating with the inflation lumen 20 through an opening 36 in an outer wall of the shaft 14.

The first connector 16 has a recess 38 to receive a proximal end 40 of the shaft 14, such that the first connector 16 may be secured to the shaft 14 through suitable means, such as adhesive. The first connector 16 has a bore 42 extending through the first connector 16 and defining a proximal portion of the inflation lumen 20, with a tubular extension 44 extending from a proximal face 46 of the first connector 16 defining a proximal end of the inflation lumen 20. The first connector 16 also has a membrane 48 of suitable elastic and flexible material, such as rubber, connected to the tubular extension 44 and extending across the bore 42 at the proximal end of the tubular extension 44 in order to close the proximal end of the inflation lumen 20. The first connector 16 has valve means 50 of known type communicating with the inflation lumen 20 through a side channel 52. When a syringe is attached to the valve means 50, the valve means 50 permits passage of liquid from the syringe through the valve means 50 in order to fill the inflation lumen 20 and cavity 34 with the liquid while inflating the balloon 20. Also, the liquid in the inflation lumen 20 may be removed through the valve means 50 by use of the syringe.

With reference to FIGS. 1-5, the shaft assembly 12 has spaced first and second conductive ECG electrodes 54 and 56 extending circumferentially around the balloon 28 on an outer surface of the balloon, with the proximal first electrode 54 having a conductive lead or plate 58 extending from the electrode 54 to a proximal end of the balloon 28, and with the second distal electrode 56 having an associated lead or plate 60 of conductive material extending from the electrode 56 to a distal end of the balloon 28. The electrodes 54 and 56 and leads 58 and 60 may be made of a suitable conductive material, such as metallic paint placed on the outer surface of the balloon 28. The first connector 16 has recesses in the proximal face 46 of the first connector 16 to receive sockets 62 and 64 of conductive material, such as metal. The shaft assembly 12 has a conductive lead 66 connected to the socket 62 and extending through the first connector 16 and the sidewall of the shaft 14 to the distal end of the balloon 28 where it is connected to the distal end of the lead 60 in order to establish electrical connection between the socket 62 and the second electrode 56. The shaft assembly 12 also has a conductive lead 68 connected to the socket 64 and extending through the first connector 16 and the wall of the shaft 14 to the proximal end of the balloon 28 where it is connected to the proximal end of the lead 58 in order to establish electrical connection between the first electrode 54 and the socket 64.

Figure 4:
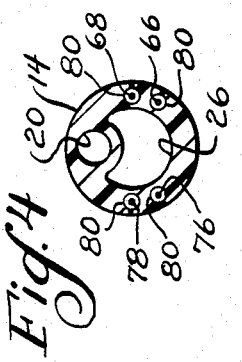
FIGS. 3 and 4 are sectional views taken substantially as indicated along the line 3,4—3,4 of FIG. 2.
Figure 3:
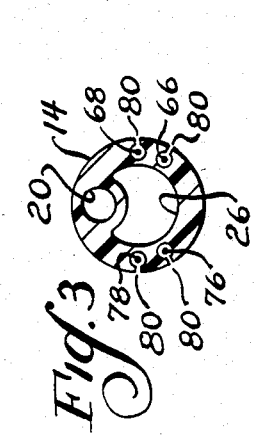

As shown, the shaft assembly 12 has a temperature sensor 70 in the second shaft lumen 26 adjacent the distal end 22 of the shaft 14. The first connector 16 has a pair of recesses in the proximal face 46 of the first connector 16 to receive a pair of conductive sockets 72 and 74, such as metal. The shaft assembly 12 also has a pair of conductive leads 76 and 78 connected to the sockets 72 and 74, respectively, and extending through the first connector 16 and through the wall of the shaft 14 to the temperature sensor 70. In this manner, electrical connection is made between the sensor 70 and the sockets 72 and 74. With reference to FIG. 3, the shaft 14 has a plurality of grooves 80 extending longitudinally through the shaft in which the leads 66, 68, 76, and 78 may be placed after which the grooves 80 may be closed in a suitable manner, such as by adhesive as shown in FIG. 4, or by heat sealing the outer portion of the shaft 14 together in the region of the grooves 80. The shaft 14 may be made of suitable plastic material, such as polyvinylchloride, and the balloon 28 may be made of suitable elastic material, such as rubber. The first and second connectors 16 and 18 may also be made of suitable plastic material, such as polyvinylchloride.

With reference to FIGS. 1 and 2, the second connector 18 has a central cavity 82 to receive a vibration detection device 84, such as a microphone or hydrophone, hereinafter microphone. The second connector 18 also has a recess 86 extending from the microphone 84 to a distal face 88 of the second connector 18 to receive the tubular extension 44. The second connector 18 has a pair of conductive pins 90 and 92 extending from the distal face 88 of the second connector 18 and receivable in the sockets 62 and 64, respectively, with the second connector 18 having a pair of conductive leads 94 and 96 extending from the pins 90 and 92, respectively, through the second connector 18 to a proximal end thereof. The second connector 18 also has a pair of conductive pins 98 and 100 extending from the distal face 88 of the second connector 18 and receivable in the sockets 72 and 74, respectively, with the second connector 18 having a pair of conductive leads 102 and 104 extending from the pins 98 and 100, respectively, through the second connector 18 to a proximal end thereof. The second connector 18 also has a pair of conductive leads 106 and 108 extending from the microphone 84 through the second connector 18 to a proximal end of the second connector 18. The proximal ends of the leads 94, 96, 102, 104, 106, and 108 may be formed into a cable connected to the proximal end of the second connector 18.

When the second connector 18 is attached to the first connector 16, the pins 90, 92, 98, and 100 are frictionally received in the sockets 62, 64, 72, and 74, respectively, in order to establish electrical contact between the pins and sockets and releasably attach the second connector 18 to the first connector 16. In the attached configuration of the connectors, the pins and sockets establish electrical connection between the lead 94 and the second electrode 56 through the leads 66 and 60, between the lead 96 and the first electrode 54 through the leads 68 and 58, and between the leads 102 and 104 and the temperature sensor 70 through the leads 76 and 78. In this manner, electrical connection is made between the second connector 18 and the electrical components in the shaft assembly 12. Also, as shown in FIG. 2, when the second connector 18 is attached to the first connector 16, the membrane 48 which closes the proximal end of the inflation lumen 20 is located adjacent the microphone 84. Thus, sounds occurring adjacent the balloon 28 are trahsmitted by the liquid in the cavity 34 and inflation lumen 20 to the membrane 48 and the microphone 84. In this manner, sounds are detected by the microphone 84 when the probe is located in the patient's body.

In use, the shaft 14 of the probe 10 is inserted into the esophagus of a patient with the balloon in an uninflated condition. Next, a syringe is attached to the valve means 50, and liquid is pumped from the syringe through the valve means 50 into the inflation lumen 20 in order to fill the inflation lumen 20 and the cavity 34 while inflating the balloon 28. The leads 106 and 108 associated with the microphone 84 may be attached to suitable electrical equipment for monitoring sounds, with the sounds being transmitted through the sound conducting medium of the liquid in the cavity 34 and inflation lumen 20 in order to monitor heart and lung sounds occurring adjacent the inflatable balloon 28. Also, the leads 94 and 96, which are electrically connected to the first and second electrodes 54 and 56, may be connected to suitable ECG electrical monitoring equipment. Similarly, the leads 102 and 104, which are electrically connected to the temperature sensor 70, may be connected to suitable electrical equipment to indicate the temperature in the patient's body.

After use of the probe 10 in the patient's body, the shaft 14 may be removed from the esophagus, and the first connector 16 of the shaft assembly 12 may be removed from the second connector 18, after which the used shaft assembly 12 may be discarded. The second connector 18 may then be attached to another shaft assembly 12 of the same type in order to use the esophageal probe 10 on another patient. In this manner, the shaft assembly 12 is rendered disposable, while the relatively expensive microphone 84 in the second connector 18 may be utilized with a number of shaft assemblies 12 on different patients. Also, placement of the microphone 84 in the second connector 18 permits use of a shaft 14 of reduced external dimensions for insertion into the patient's body as compared to a shaft in which the microphone is located in the shaft itself.

The foregoing detailed description is given for clearness of understanding only, and no unnecessary limitations should be understood therefrom, as modifications will be obvious to those skilled in the art.

I claim:

1. An esophageal probe comprising:
    a shaft assembly comprising an elongated shaft having a distal end, a proximal end, an opening adjacent said distal end, an inflation lumen extending through the shaft, the lumen communicating with the opening, an inflatable balloon extending around a distal portion of the shaft and defining a cavity communicating with the opening and thus the inflation lumen, means closing the lumen at the distal end of the shaft, a flexible membrane attached to and closing the lumen at the proximal end of the shaft, a fluid sound transmitting medium filling said lumen and said balloon, inflation means comprising valve means on the shaft communicating with the inflation lumen to permit passage of the fluid into the inflation lumen to fill the lumen and inflate the balloon, the sound transmitting medium being sealed within the shaft by the lumen, membrane, balloon, valve means and means closing the lumen at the distal end of the probe, a connector at the proximal end of the shaft, at least one conductive electrode on a distal portion of the shaft, and first conductor means electrically connecting the electrode with the connector at the proximal end of the shaft;

a second connector releasably attached to the first connector and having a proximal end, a distal end, an electrical sound detection device encased therein; and second electrical conductor means therein terminating at the second connector distal end; and quick disconnect means for releasably attaching the second connector to the first connector and for simultaneously establishing electrical connection between the first and second conductor means, the quick disconnect means comprising mating means on the shaft proximal end and the second connector distal end, the flexible membrane on the proximal end of the shaft and the electrical sound detection device in the second connector being so located as to be in face to face contact when the first and second connectors are attached together by the quick disconnect means, whereby, in use, heart and/or lung sounds of a patient acoustically sensed by the sound transmitting medium are transmitted directly to the flexible membrane and thus directly to the sound detection device, for conversion into electrical signals which may be further transmitted and converted into intelligible information, and further whereby, after use, said shaft assembly may be discarded and substituted with another shaft assembly of similar construction for use on another or the same patient.

2. The probe of claim 1 wherein the vibration detection device comprises a microphone.

3. The probe of claim 1 wherein the quick disconnect mating means comprises a plurality of conductive sockets in one of the connectors and a plurality of conductive pins extending from the other of said connectors, with said pins being receivable in said sockets when the second connector is attached to the first connector.

4. The probe of claim 1 wherein the sound transmitting medium comprises a liquid.

* * * * *